US00PP22638P2

(12) United States Plant Patent
Blom

(10) Patent No.: US PP22,638 P2
(45) Date of Patent: Apr. 10, 2012

(54) ***CHRYSANTHEMUM* PLANT NAMED 'ZANMUPEARLY'**

(50) Latin Name: *Chrysanthemum×morifolium Ramat.*
Varietal Denomination: Zanmupearly

(75) Inventor: Wilhelmus Bernardus Blom, Leimuiden (NL)

(73) Assignee: Chrysanthemum Breeders Association Research B.V., Valkenburg Z-H (NL)

( * ) Notice: Subject to any disclaimer, the term of this patent is extended or adjusted under 35 U.S.C. 154(b) by 0 days.

(21) Appl. No.: 12/926,554

(22) Filed: Nov. 24, 2010

(51) Int. Cl.
*A01H 5/00* (2006.01)

(52) U.S. Cl. ..... Plt./294

(58) Field of Classification Search ..... Plt./294
See application file for complete search history.

*Primary Examiner* — Annette Para
(74) *Attorney, Agent, or Firm* — Steptoe & Johnson LLP

(57) ABSTRACT

A *chrysanthemum* plant named 'Zanmupearly' characterized by its medium sized blooms with white ray florets and a cream center, and prolific branching; natural season flower date October 10; blooming for a period of 4 weeks.

3 Drawing Sheets

Botanical designation: *Chrysanthemum×morifolium* Ramat.

Cultivar denomination: 'Zanmupearly'.

BACKGROUND OF THE INVENTION

The present invention relates to a new and distinct cultivar of *chrysanthemum* plant, botanically known as *Chrysanthemum×morifolium* Ramat., commercially known as a garden mum, and hereinafter referred to by the cultivar denomination 'Zanmupearly'. 'Zanmupearly' is a product of a breeding and selection program for outdoor pot mums (garden mums) which had the objective of creating new cultivars with a double type inflorescence, a natural season flower date around October 10, blooming for a period of 5 weeks. 'Zanmupearly' is a seedling resulting from a crossing program set up by a previous breeder, and which records are unknown to the inventor.

The new and distinct cultivar was discovered and selected as a flowering plant by Wilhelmus Bernardus Blom on a cultivated field in Rijsenhout, The Netherlands in 2003. The first act of asexual production of 'Zanmupearly' was accomplished when vegetative cuttings from the initial selection in 2003 were propagated further in a controlled environment in Rijsenhout, The Netherlands. The new cultivar has been found to retain its distinctive characteristics through successive propagations.

BRIEF DESCRIPTION OF THE DRAWINGS

The present invention of a new and distinct variety of *chrysanthemum* is shown in the accompanying drawings, the color being as nearly true as possible with color photographs of this type.

DESCRIPTION OF THE INVENTION

Figure 1:
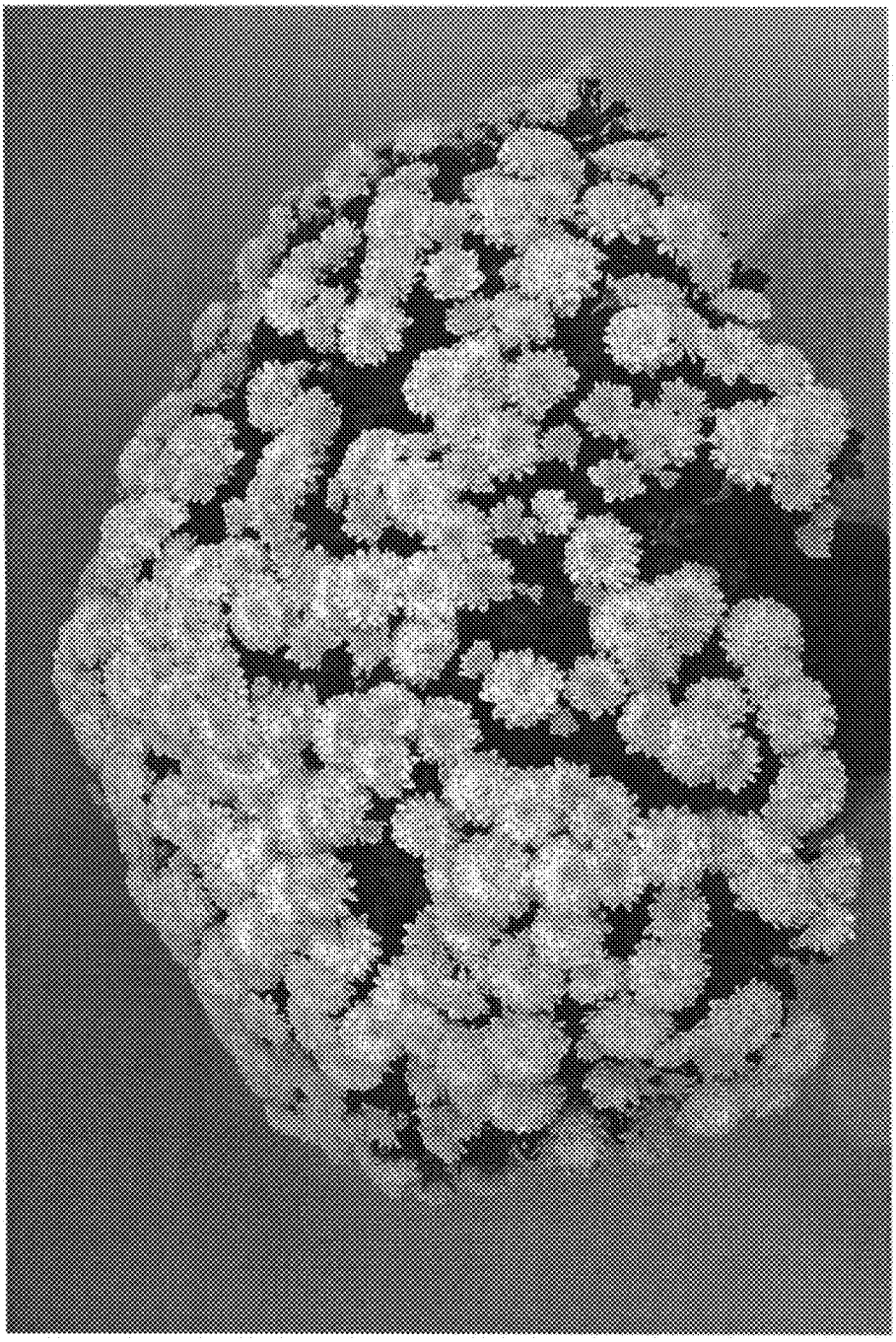
FIG. 1 shows a plant of the cultivar in full bloom.
Figure 2:
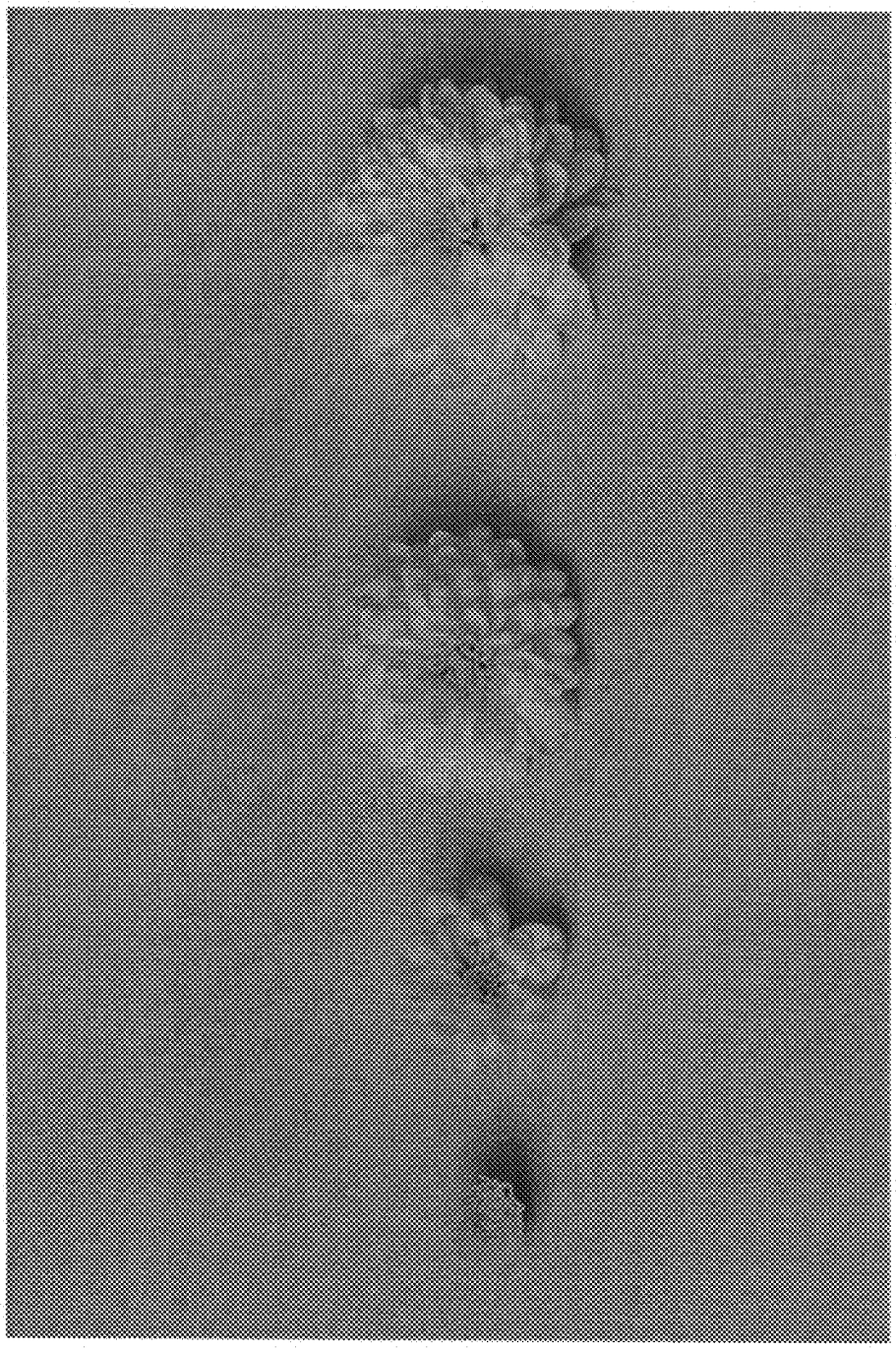
FIG. 2 shows the various stages of bloom of the new cultivar.
Figure 3:
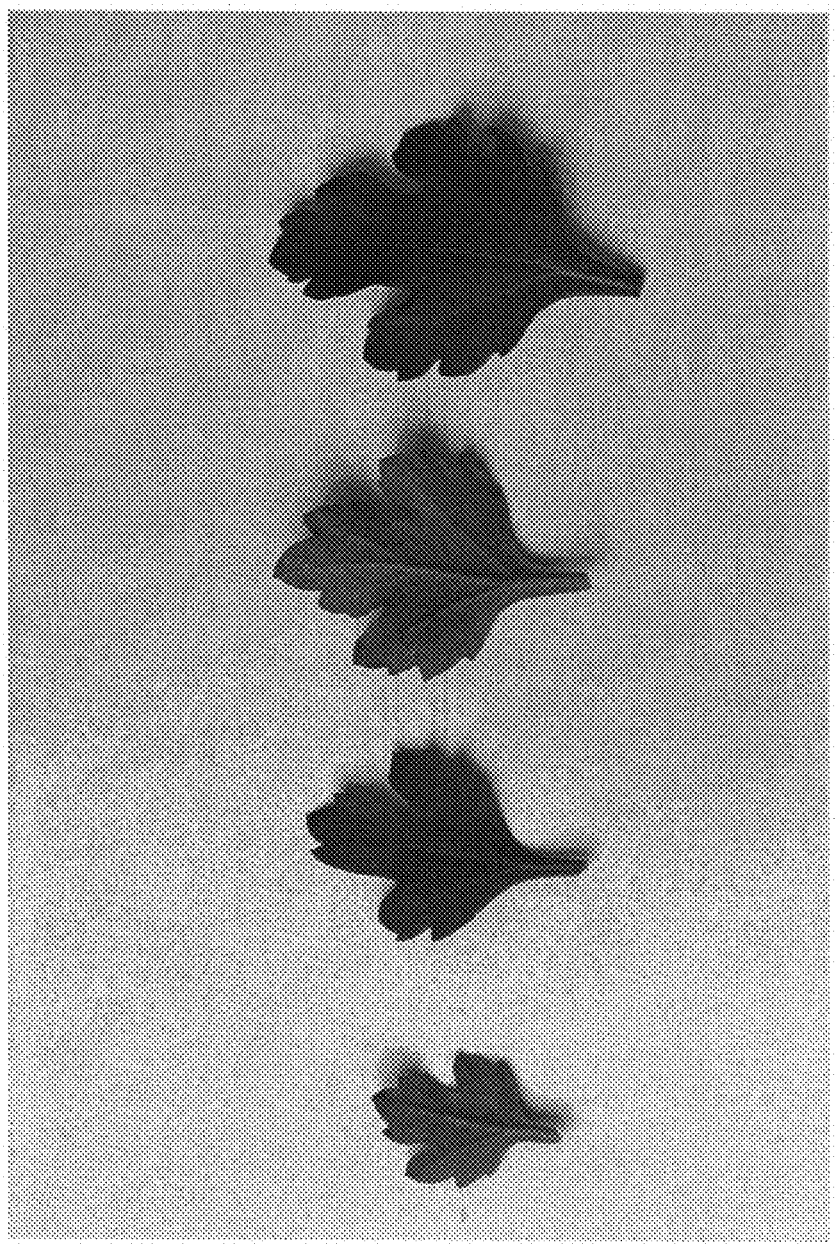
FIG. 3 shows the various stages of foliage of the new cultivar.

The observations and measurements were gathered from plants grown out door in Rijsenhout, The Netherlands under natural day length and temperature and planted in week 23 in 2009. The natural blooming date of this crop was October 11. The average height of the plants was 38 cm. No growth retardants were used. No tests were done on disease or insect resistance or susceptibility. No tests were done on cold or drought tolerance. This new variety produces medium sized blooms with white ray florets and a cream center blooming for a period of 4 weeks.

From the cultivars known to inventor the most similar existing cultivar in comparison to 'Zanmupearly' is 'Zanmucandle' (U.S. patent application Ser. No. 12/591,869). When 'Zanmucandle' and 'Zanmupearly' are being compared the following differences are noticed: (1) Inflorescence size And (2) Plant height. (1) The inflorescences of 'Zanmucandle' are larger than those of 'Zanmupearly'. (2) Plants of 'Zanmucandle' are smaller than those of 'Zanmupearly'.

The following is a description of the plant and characteristics that distinguish 'Zanmupearly' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, edition 2001.

TABLE 1

Botanical Description of *Chrysanthemum xmorifolium* Ramat. 'Zanmupearly'

| | |
|---|---|
| **Bud** | |
| Size | Small; cross-section 4 mm, height 4 mm |
| Shape | Round |
| Texture | Pubescent |
| Outside Color | Greyed-green 191A |
| **Phyllaries** | |
| Number | 22, arranged in 3 rows |
| Shape | Elliptic |
| Apex | Acute |
| Base | Truncate |
| Margin | Entire |

TABLE 1-continued

| Botanical Description of *Chrysanthemum xmorifolium* Ramat. 'Zanmupearly' | |
|---|---|
| Color | Upper surface: Greyed-green 189A |
| Length and width | 5 mm; 3 mm |
| Texture | Pubescent |
| Inflorescence | |
| Type | Double |
| Height | 1.2 cm |
| Diameter | 4.2 cm |
| Peduncle length | 5-6 cm |
| Peduncle color | Green N138 B-C |
| Peduncle diameter | 1.5 mm |
| Peduncle texture | Pubescent |
| Number per branch | Approx 6 inflorescences |
| Duration of flowering | 4 weeks |
| Seeds | Produced in small quantities, ovate, Greyed-brown 199A, length 1.5 mm, diameter 0.5 mm |
| Fragrance | Faint chrysanthemum odor |
| Color | |
| Center of inflorescence | Immature stage: Yellow 6D<br>Mature stage: White 155D |
| Color of upper surface of the ray-florets | White 155D |
| Color of the lower surface of the ray-florets | White 155D |
| Tonality from Distance | A garden mum with white blooms and a cream center |
| Color of the ray-florets after aging of the plant | White 155D |
| Ray florets | |
| Texture | Upper and lower surface smooth |
| Number | Ca. 180 |
| Shape | Elliptic |
| Apex | Pointed |
| Base | Attenuate |
| Cross-section | Flat |
| Longitudinal axis of majority | Straight to reflexing |
| Length of corolla tube | 3 mm |
| Ray-floret margin | Entire |
| Ray-floret length | 1.2-1.5 cm |
| Ray-floret width | 3-5 mm |
| Ratio length/width | Medium |
| Disc florets | Absent |
| Receptacle | |
| Color | Yellow-green 145D |
| Shape | Domed raised |
| Height | 4 mm |
| Diameter | 4 mm |
| Reproductive Organs | |
| Androecium | Absent |
| Pollen | Absent |
| Gynoecium | Present on both ray florets |
| Style color | Yellow-green 154C |
| Style Length | 3 mm |
| Stigma color | Yellow 7A |

TABLE 1-continued

| Botanical Description of *Chrysanthemum xmorifolium* Ramat. 'Zanmupearly' | |
|---|---|
| Stigma Width | 1 mm |
| Ovary | Enclosed in calyx |
| Plant | |
| Form | Grown as a spray type pot mum, outdoor raised and mounded |
| Growth habit | Spherical shape |
| Growth rate | Variable, medium to high |
| Height | 35-40 cm |
| Width | 45-60 cm |
| Stem Color | Greyed-brown 199A |
| Stem Strength | Strong |
| Stem Brittleness | Not brittle |
| Stem Anthocyanin Coloration | Not observed |
| Internode length | 1-1.5 cm |
| Length of lateral branch | From top to bottom 18 cm |
| Lateral branch color | Green 137 C |
| Lateral branch, attachment | Not brittle |
| Lateral branch diameter | 2.mm |
| Branching (average number of lateral branches) | Prolific with 8 breaks after pinching |
| Natural season blooming date | October 10 (week 41) |
| Foliage | |
| Leaf color | Upper side: Green 137B<br>Lower side: Green 138B |
| Color midvein | Upper side: Yellow-green 147D<br>Lower side: Yellow-green 148D |
| Size | Small; length 3-4 cm, width 2-3 cm |
| Quantity (number per lateral branch) | Ca. 22 |
| Shape | Broadly elliptic |
| Texture upper side | Sparsely pubescent |
| Texture under side | Pubescent |
| Venation arrangement | Palmate |
| Shape of the margin | Serrated |
| Shape of Base of Sinus Between Lateral Lobes | Rounded |
| Margin of Sinus Between Lateral Lobes | Diverging |
| Shape of Base | Attenuate to truncate |
| Apex | Mucronulate |
| Petiole length | 0.8-1.2 cm |
| Petiole diameter | 2 mm |
| Petiole color | Yellow-green 147D |

TABLE 2

| Differences with the comparison variety (when grown side to side) | | |
|---|---|---|
| | "Zanmupearly" | 'Zanmucandle' |
| Inflorescence size | 4.2 cm | 6.5 cm |
| Plant height | 38 cm | 16 cm |

I claim:

1. A new and distinct *chrysanthemum* plant named 'Zanmupearly' as described and illustrated.

* * * * *